United States Patent
Brand et al.

(10) Patent No.: US 7,687,667 B2
(45) Date of Patent: Mar. 30, 2010

(54) CATALYST FOR THE PRODUCTION OF METHYL MERCAPTAN FROM METHANOL AND HYDROGEN SULFIDE

(75) Inventors: Alexandra Brand, Darmstadt (DE); Veronika Quaschning, Mannheim (DE)

(73) Assignee: BASF SE, Ludwigshafen (DE)

( * ) Notice: Subject to any disclaimer, the term of this patent is extended or adjusted under 35 U.S.C. 154(b) by 616 days.

(21) Appl. No.: 10/554,701

(22) PCT Filed: Apr. 23, 2004

(86) PCT No.: PCT/EP2004/004344
§ 371 (c)(1),
(2), (4) Date: Oct. 27, 2005

(87) PCT Pub. No.: WO2004/096760
PCT Pub. Date: Nov. 11, 2004

(65) Prior Publication Data
US 2007/0015941 A1    Jan. 18, 2007

(30) Foreign Application Priority Data
Apr. 30, 2003   (DE) ............................. 103 19 739

(51) Int. Cl.
*C07C 319/00* (2006.01)
(52) U.S. Cl. .................... 568/71; 502/208; 502/305; 502/355
(58) Field of Classification Search .............. 568/71; 502/208, 305, 355
See application file for complete search history.

(56) References Cited

U.S. PATENT DOCUMENTS

| | | | |
|---|---|---|---|
| 2,647,151 A | | 7/1953 | Bell |
| 2,685,605 A | | 8/1954 | Bell |
| 3,935,276 A | * | 1/1976 | Biola et al. .................. 568/71 |
| 5,283,369 A | * | 2/1994 | Clark et al. .................. 568/71 |
| 5,847,223 A | | 12/1998 | Ponceblanc et al. |
| 5,852,219 A | * | 12/1998 | Sauer et al. .................. 568/71 |
| 5,874,630 A | | 2/1999 | Cook et al. |
| 5,977,011 A | * | 11/1999 | Sauer et al. .................. 502/305 |
| 6,198,003 B1 | * | 3/2001 | Lin et al. .................. 568/71 |

FOREIGN PATENT DOCUMENTS

| | | |
|---|---|---|
| DE | 101 37 773 A1 | 2/2003 |
| EP | 0 832 878 A2 | 4/1998 |
| RU | 2 056 940 C1 | 3/1996 |
| SU | 1 316 127 A1 | 10/1996 |
| SU | 1 608 923 A1 | 11/1996 |
| WO | WO-99/14172 A2 | 3/1999 |

OTHER PUBLICATIONS

Mashkina et al., Activity of tungstate catalysts in the synthesis of methyl mercaptan from methanol and hydrogen sulfide; Reaction Kinetics and Catalysis Letters (1988), 36(1), 159-164.*
"Effect of Acid-Base Properties of Catalysts on their Activity in Methymercaptane Synthesis" by Mashkina et al., *React. Kinet. Catal. Lett.*, vol. 34, No. 2, 1987, pp. 407-412.
"Activity of Tungstate Catalysts in the Synthesis of Methyl-Mercaptane from Methanol and Hydrogen Sulfide" by Mashkina et al., *React. Kinet. Catal. Lett.*, vol. 36, No. 1, 1988, pp. 159-164.

* cited by examiner

*Primary Examiner*—Daniel M Sullivan
*Assistant Examiner*—Chukwuma O Nwaonicha
(74) *Attorney, Agent, or Firm*—Connolly Bove Lodge & Hutz LLP

(57) ABSTRACT

The invention relates to a catalyst for the synthesis of methyl mercaptan from hydrogen sulfide and methanol and to a process for preparing methyl mercaptans. The catalyst comprises active aluminum oxide on which an alkali metal tungstate and ammonium salts have been deposited.

20 Claims, No Drawings

CATALYST FOR THE PRODUCTION OF METHYL MERCAPTAN FROM METHANOL AND HYDROGEN SULFIDE

This application is a National Stage of PCT/EP2004/004344 filed Apr. 23, 2004 which in turn claims priority from German Application 103 19 739.7, filed Apr. 30, 2003.

The present invention relates to a catalyst for preparing methyl mercaptan from methanol and hydrogen sulfide.

Methyl mercaptan is an important intermediate for the synthesis of methionine, for the preparation of dimethyl sulfoxide and dimethyl sulfone or for the synthesis of alkanesulfonic acids. Methyl mercaptan is at present prepared predominantly by reaction of hydrogen sulfide and methanol in the gas phase over a catalyst comprising aluminum oxide. The synthesis of methyl mercaptan is usually carried out at from 300 to 500° C. and pressures of from 1 to 25 bar.

To increase the activity and selectivity of the aluminum oxide catalyst, this is customarily doped with an alkali metal tungstate (cf., for example, EP-A-832 878). Mashkina et al. state that catalysts which comprise acid centers on the surface are very active but give equal yields of methyl mercaptan and dimethyl sulfide. Catalysts which have strongly basic centers are less active, but display a higher selectivity to methyl mercaptan (Mashkina et al., React. Kinet. Catal. Lett. 1987, 407-412). The increases in activity and selectivity are thus explained by the presence of both basic and acidic reaction centers. However, the aluminum oxide is also doped with other substances, for example with an alkali metal carbonate (U.S. Pat. No. 5,847,223).

An improvement in activity and selectivity is also obtained by increasing the molar ratio of hydrogen sulfide to alcohol. Molar ratios in the range from 1 to 10 are customarily employed. However, a high molar ratio of from 10 to 3 also means a large excess of hydrogen sulfide in the reaction gas mixture and thus makes it necessary to circulate large amounts of gas.

U.S. Pat. No. 2,685,605 relates to a process for preparing methyl mercaptan by reacting hydrogen sulfide and methanol over a catalyst, preferably a thorium/pumice catalyst, with small amounts of water being introduced into the reactor together with the hydrogen sulfide and the methanol.

U.S. Pat. No. 2,647,151 describes the preparation of alkyl mercaptans by reaction of hydrogen sulfide and alcohol over a thorium/pumice catalyst, in which the formation of the desired alkyl mercaptans is said to be increased by suppressing the formation of organic sulfides formed as by-products. This increase in selectivity is achieved by introducing small amounts of hydrogen into the reactor.

DE-A-101 37 773 teaches introduction of oxygen into the reactor together with the alcohol and hydrogen sulfide while the reaction is proceeding in the presence of a catalyst comprising aluminum oxide and potassium tungstate. The addition of oxygen reduces troublesome deposits on the catalyst and regeneration occurs during the process.

U.S. Pat. No. 3,935,376 describes a process whose improvement comprises optimization of the temperature conditions, resulting in minimization of catalyst quality decreases and by-products. The catalyst comprises aluminum oxide and a promoter. It is disclosed that it is possible to keep the temperature in the entire region at an optimal level when at least three catalyst zones are created. The total amount of hydrogen sulfide is introduced into the first catalyst zone, while the addition of methanol can be distributed over all the catalyst zones. The ratio of hydrogen sulfide to methanol is in the range from 1.1 to 2.5.

EP-A-832 878 describes improved catalysts which are obtainable by depositing the potassium tungstate promoter in two portions onto the active aluminum oxide by means of a specific procedure. Furthermore, the catalysts are presulfided under conditions similar to the reaction conditions.

Mashkina et al. (React. Kinet. Catal. Lett. 1988, 159-164) modified the form in which the promoter was employed, using heptatungstate, dodecatungstate and metatungstate. Furthermore, ammonium tungstate doped with potassium carbonate, potassium tungstate with a small addition of acid and/or with addition of silicon oxide were used. The result of this comprehensive study was that simple potassium tungstate doping without further addition of promoters or treatment gave the best results in terms of the selectivity to methyl mercaptan and the reaction rate.

In SU 1316127, SU 1608923, RU 2056940 and WO 99/14172, it was found that an increased selectivity is obtained when using aluminum borate supports or by addition of boron oxides to the tungstate promoter or by means of a mixture of promoters comprising potassium aluminate, amorphous tungsten oxide and sodium oxide and/or boron oxide.

The catalysts and methods of preparing methyl mercaptan known from the prior art are still in need of improvement with regard to the selectivity and activity and economical process conditions.

It is therefore an object of the present invention to provide a very active and selective methyl mercaptan catalyst without a multistage preparation of the catalyst, introduction of expensive or toxic active compositions or any particular mode of operation of the reactor being necessary. Furthermore, the ratio of hydrogen sulfide to alcohol should deviate little from 1 in order to reduce the energy consumption required.

We have found that this object is achieved by a catalyst which is obtainable by applying an alkali metal tungstate and at least one ammonium salt and/or at least one protic acid selected from the group consisting of sulfuric acid, phosphoric acid, sulfurous acid, tungstic acid, phosphorous acid, hypophosphorous acid, hydrogen fluoride, hydrogen bromide and hydrogen iodide as promoters to active aluminum oxide. Furthermore, it has been found that methyl mercaptan can be prepared advantageously using the catalyst of the present invention. As alkali metal tungstate, preference is given to using potassium tungstate. The tungstate is advantageously applied in an amount of from 1 to 20% by weight, preferably from 10 to 16% by weight, based on the total mass of the catalyst.

Preference is given to using ammonium salts. Ammonium salts which can be used are, in particular, sulfates, phosphates, sulfides, tungstates, molybdates, sulfites, peroxodisulfates, phosphites, hypophosphites, halides and carbonates. Preference is given to sulfates, phosphates, sulfides, tungstates, molybdates, sulfites, peroxodisulfates, phosphites and hypophosphites. Particular preference is given to sulfur- or phosphorus-comprising salts and also tungstate salts. Mixtures of ammonium salts are likewise possible. It is advantageous to apply from 0.01 to 15% by weight, in particular from 0.01 to 10% by weight, of ammonium salts, based on the total mass of the catalyst.

Instead of ammonium salts or in admixture with these salts, the use of protic acids selected from the group consisting of sulfuric acid, phosphoric acid, sulfurous acid, tungstic acid, phosphorous acid and hypophosphorous acid is also conceivable. Particular preference is given to sulfur- or phosphorus-comprising protic acids.

This catalyst is, according to the present invention, obtainable by impregnating the activated aluminum oxide with the promoter mixture comprising alkali metal tungstate and ammonium salts or spraying this promoter mixture onto the aluminum oxide catalyst. Impregnation can be carried out according to the water uptake, i.e. the amount of solution corresponds to the pore volume of the support, or by steeping in an excess of solution, i.e. the solution volume is greater than the pore volume. The alkali metal tungstate can likewise be prepared by reaction of tungstate salts, for example ammonium tungstate, ammonium metatungstate or ammonium paratungstate, in each case in the form of the hydrates, or tungstic acid with, for example, potassium hydroxide or sodium hydroxide prior to application. The catalyst is subsequently calcined in air or in the presence of oxygen, e.g. at from 400 to 500° C.

The preparation is thus a simple single-stage process. If appropriate, the aluminum oxide can be calcined at from 300 to 600° C., preferably from 400 to 500° C., for from 1 to 10 hours, preferably 1 to 5 hours, prior to application of the promoters.

The catalyst obtained advantageously has a pH of less than 9.8, in particular a pH in the range from 5 to 9.7. The pH measurement is carried out by preparing a 10% strength aqueous suspension of the catalyst to be examined. This sample is shaken for one minute, allowed to stand for 5 minutes and the pH of the suspension is subsequently measured by means of a pH electrode.

Compared to the catalysts described in the prior art, this catalyst leads to a higher activity and selectivity of the finished catalyst, in particular at a low molar ratio of hydrogen sulfide to methanol of from 3 to 1.

As aluminum oxide for this catalyst, it is advantageous to use active aluminum oxide. This material has a high specific surface area in the range from about 10 to 400 m$^2$/g and comprises mainly oxides of the transition series of crystallographic phases of aluminum oxide (cf., for example, Ullmann's Encyclopedia of Industrial Chemistry of 1985, Vol. A1, pages 561-562). These transition oxides include χ-, κ-, γ-, δ-, η-, θ-aluminum oxide. Active aluminum oxide is marketed commercially in various grades and physical forms for catalytic applications. A well suited type is, for example, γ-aluminum oxide in granulated or extruded form. It is advantageous to use aluminum oxide having extrudate diameters of from 1 to 5 mm. The specific surface area is preferably in the range from 150 to 400 m$^2$/g. The total pore volume is in the range from 0.3 to 1.0 ml/g. The bulk density is in the range from 300 to 1000 g/l.

The catalyst can, if appropriate, be presulfided under conditions similar to those of the methyl mercaptan synthesis before it is used in the synthesis. For this purpose, a stream of hydrogen sulfide is passed over the catalyst particles at from 200 to 450° C. and a pressure of from 1 to 25 bar for from 0.5 to 100 hours.

The molar ratio of hydrogen sulfide to methanol in the methyl mercaptan synthesis is generally from 1:1 to 10:1, preferably from 1:1 to 2:1. The molar ratios indicated comprise both the freshly added hydrogen sulfide and methanol and also any recycled hydrogen sulfide and methanol.

The catalyst is advantageously installed in the reactor in the form of solid particles having a diameter of from 1 to 5 mm, for example 4 mm.

The reactor feed can further comprise oxygen, water or hydrogen and also an inert gas or a mixture of inert gases in addition to hydrogen sulfide and alcohol. In general, the reactor feed comprises from 0 to 30 mol, preferably from 5 to 30 mol, of inert gas per mole of alcohol. Suitable inert gases are, for example, nitrogen, methane, ethane, propane, butane and/or carbon dioxide. Troublesome deposits on the catalyst can be avoided by addition of oxygen. In this way, regeneration of the catalyst can occur during the process. The oxygen concentration in the process is generally <2.5% by weight, based on the amount of reactor feed, and is thus far below the explosive limits. The oxygen concentration is preferably from 10 ppm to 0.5% by weight, particularly preferably from 10 ppm to 500 ppm. The oxygen can be introduced into the reactor in various forms. It is possible to use pure oxygen, if appropriate in admixture with inert gas. The oxygen is usually added in the form of air. The reactor feed can further comprise recirculated sulfur-comprising components which have been separated off from the methyl mercaptan produced (as described, for example, in DE-A-1768826).

The process of the present invention for preparing methyl mercaptan by reaction of hydrogen sulfide and methanol over a catalyst is generally carried out as a gas-phase reaction in a tube reactor. It is also possible for a plurality of tube reactors to be connected in series. In general, methanol and hydrogen sulfide are heated to a temperature which is high enough for both methanol and methyl mercaptan to be present in the vapor phase but is below the decomposition temperature of methyl mercaptan. In general, the process of the present invention is carried out at from 250 to 500° C., preferably from 300 to 450° C. The precise reaction temperature is dependent, inter alia, on the reaction pressure and the catalyst used.

The process of the present invention is generally carried out at a pressure of from 1 to 25 bar. Of course, the pressure is kept below that at which the reactor feed or the methyl mercaptan would condense. The pressure in the process of the present invention is preferably from 1 to 10 bar. To reduce the emission risk, it can be set to from 1 to 3 bar, preferably close to atmospheric pressure.

The process of the present invention is generally carried out continuously. The work-up of the methyl mercaptan obtained is carried out by methods known to those skilled in the art.

The WHSV (weight hourly space velocity=weight of starting materials/weight of catalyst per tube and hour) is generally from 0.1 to 10 h$^{-1}$, preferably from 0.1 to 5 h$^{-1}$, particularly preferably from 0.5 to 2 h$^{-1}$.

The conversion in the process of the present invention is generally from 80 to 100%, preferably from 95 to 100%, based on the amount of the component used in a submolar amount (i.e. based on methanol in the methyl mercaptan synthesis). A methyl mercaptan selectivity of from 80 to 100% can be achieved by means of the process of the present invention.

EXAMPLES

Example 1

Preparation of Comparative Catalyst (14% by Weight of K$_2$WO$_4$ on γ-Al$_2$O$_3$)

203 g of ammonium metatungstate hydrate were dissolved in 0.385 l of water, 182 g of a 48% strength aqueous solution of potassium hydroxide were then added and the solution was subsequently made up to a volume corresponding to the water uptake of the support. This 1.048 l of impregnation solution was sprayed uniformly onto 1.588 kg of γ-Al$_2$O$_3$ extrudates. The catalyst was finally calcined for 2 hours at 450° C. in a convection furnace.

Preparation of the catalyst according to the present invention from aluminum oxide, potassium tungstate and ammonium salts

Example 2

Ammonium Phosphate 72.3 g of ammonium metatungstate hydrate were dissolved in 0.150 l of water, and 29.7 g of potassium hydroxide and 88.3 g of ammonium phosphate trihydrate were then added. This solution was made up to a volume corresponding to the water uptake of the support. The impregnation solution was applied uniformly to 500 g of γ-$Al_2O_3$ extrudates and the catalyst was finally calcined for 2 hours at 450° C. in a convection furnace.

Example 3

Ammonium Sulfate

Using a method analogous to Example 2, an aqueous solution was prepared from ammonium metatungstate hydrate, potassium hydroxide and 30.9 g of ammonium sulfate, applied to 500 g of γ-$Al_2O_3$ extrudates and the catalyst was finally calcined for 2 hours at 450° C. in a convection furnace.

Example 4

Ammonium Sulfide

Using a method analogous to Example 2, an aqueous solution was prepared from ammonium metatungstate hydrate, potassium hydroxide and 36.1 g of ammonium sulfide, applied to 500 g of γ-$Al_2O_3$ extrudates and the catalyst was finally calcined for 2 hours at 450° C. in a convection furnace.

Characterization of the Catalysts pH measurement: A 10% aqueous suspension was prepared from the catalyst to be examined. The sample was shaken for one minute, allowed to stand for 5 minutes and the pH of the suspension was subsequently measured using a pH electrode.

$A_{BET}$ Measurement: DIN 66131

Performance Test:

The MeSH reactor (length: 600 mm, diameter: 25 mm) was charged with 280 g of catalyst extrudates. At 390° C. (middle of the reactor) and a pressure of 1.1 bar, 48 g/h (1.5 mol) of gaseous methanol and 64 g/h (1.9 mol) of hydrogen sulfide were fed into the tube reactor. The composition of the gas was determined by gas chromatography.

| Example | Hot spot temp. [° C.] | Decomposition products [GC % by area] | Selectivity [%] | MeOH conversion [%] | MeSH yield [%] |
|---|---|---|---|---|---|
| Comp. Ex. 1 | 432 | 1.10 | 83.8 | 97.7 | 81.9 |
| Ex. 2 | 440 | 1.78 | 89 | 99 | 89 |
| Ex. 3 | 440 | 1.44 | 89 | 97 | 87 |
| Ex. 4 | 443 | 1.38 | 88 | 97 | 86 |

We claim:

1. A catalyst for the synthesis of methyl mercaptan, obtainable from aluminum oxide, an alkali metal tungstate and at least one further component selected from the groups of the ammonium salts and of the protic acids sulfuric acid, phosphoric acid, sulfurous acid, tungstic acid, phosphorous acid, hypophosphorous acid, or a mixture thereof, wherein the pH of the catalyst, measured on a 10% strength aqueous suspension, is in the range from 5.0 to 9.7.

2. The catalyst according to claim 1 which is obtainable from aluminum oxide, an alkali metal tungstate and at least one ammonium salt.

3. The catalyst according to claim 1, wherein the alkali metal tungstate used is a potassium tungstate.

4. The catalyst according to claim 1, wherein ammonium salts used are sulfates, phosphates, sulfides, tungstates, molybdates, sulfites, peroxodisulfates, phosphites and hypophosphites.

5. The catalyst according to claim 1, wherein ammonium salts used are sulfur- or phosphorus-comprising salts or tungstate salts.

6. The catalyst according to claim 1, wherein alkali metal tungstates are applied in an amount of from 10 to 16% by weight, based on the total mass of the catalyst.

| Catalyst | Promoters | | $A_{BET}$ [m²/g] | pH | Chem. analysis [% by weight] |
|---|---|---|---|---|---|
| | Type | Amount [% by weight] | | | |
| Comp. Ex. 1 | — | — | 221 | 9.8 | — |
| Ex. 2 | Ammonium phosphate | 5% of $P_2O_5$ | 162 | 7.9 | P: 2.2 |
| Ex. 3 | Ammonium sulfate | 5% of $(NH_4)_2SO_4$ | 190 | 6.0 | S: 1.1 |
| Ex. 4 | Ammonium sulfide | 3% of $(NH_4)_2S$ | 189 | 8.2 | S: 0.4 |

7. The catalyst according to claim 1, wherein ammonium salts are applied in an amount of from 0.01 to 15% by weight, based on the total mass of the catalyst.

8. A process for preparing methyl mercaptams by reacting methanol with hydrogen sulfide, wherein a catalyst according to claim 1 is used.

9. The process according to claim 8, wherein hydrogen sulfide and methanol are used in a molar ratio of from 1:1 to 2:1 in the preparation of methyl mercaptams.

10. The catalyst according to claim 2, wherein the alkali metal tungstate used is a potassium tungstate.

11. The catalyst according to claim 2, wherein ammonium salts used are sulfates, phosphates, sulfides, tungstates, molybdates, sulfites, peroxodisulfates, phosphites and hypophosphites.

12. The catalyst according to claim 2, wherein ammonium salts used are sulfur- or phosphorus-comprising salts or tungstate salts.

13. The catalyst according to claim 2, wherein alkali metal tungstates are applied in an amount of from 10 to 16% by weight, based on the total mass of the catalyst.

14. The catalyst according to claim 2, wherein ammonium salts are applied in an amount of from 0.01 to 15% by weight, based on the total mass of the catalyst.

15. A process for preparing methyl mercaptams by reacting methanol with hydrogen sulfide, wherein a catalyst according to claim 2 is used.

16. A process for preparing methyl mercaptams by reacting methanol with hydrogen sulfide, wherein a catalyst according to claim 3 is used.

17. A process for preparing methyl mercaptams by reacting methanol with hydrogen sulfide, wherein a catalyst according to claim 4 is used.

18. A process for preparing methyl mercaptams by reacting methanol with hydrogen sulfide, wherein a catalyst according to claim 5 is used.

19. A process for preparing methyl mercaptams by reacting methanol with hydrogen sulfide, wherein a catalyst according to claim 6 is used.

20. A process for preparing methyl mercaptams by reacting methanol with hydrogen sulfide, wherein a catalyst according to claim 7 is used.

\* \* \* \* \*